(12) United States Patent
Truckai et al.

(10) Patent No.: US 12,667,381 B2
(45) Date of Patent: Jun. 30, 2026

(54) RESECTION DEVICE WITH RAZOR-LIKE CUTTING EDGES

(71) Applicant: Meditrina, Inc., San Jose, CA (US)

(72) Inventors: Tamas J. Truckai, Saratoga, CA (US); John H. Shadduck, Menlo Park, CA (US)

(73) Assignee: Meditrina, Inc., San Jose, CA (US)

( * ) Notice: Subject to any disclaimer, the term of this patent is extended or adjusted under 35 U.S.C. 154(b) by 1213 days.

(21) Appl. No.: 17/303,657

(22) Filed: Jun. 3, 2021

(65) Prior Publication Data

US 2022/0387060 A1 Dec. 8, 2022

(51) Int. Cl.
*A61B 17/32* (2006.01)

(52) U.S. Cl.
CPC .............................. *A61B 17/32002* (2013.01)

(58) Field of Classification Search
CPC .......... A61B 17/32002; A61B 17/3201; A61B 17/144; A61B 17/142; A61B 2017/320032; A61B 2017/320024
See application file for complete search history.

(56) References Cited

U.S. PATENT DOCUMENTS

| | | | |
|---|---|---|---|
| 4,815,642 A | 3/1989 | Ray | |
| 5,423,845 A | 6/1995 | Mcdaniel | |
| 6,053,928 A * | 4/2000 | Van Wyk | A61B 17/32002 |
| | | | 606/167 |

| | | | |
|---|---|---|---|
| 6,342,061 B1 | 1/2002 | Kauker et al. | |
| 8,313,502 B2 | 11/2012 | Heisler | |
| 9,839,441 B2 | 12/2017 | Hayes et al. | |
| 12,029,445 B2 | 7/2024 | Truckai et al. | |
| 12,029,455 B2 | 7/2024 | Gokcen et al. | |
| 2006/0196038 A1 | 9/2006 | Van Wyk | |
| 2006/0212060 A1 * | 9/2006 | Hacker .......... A61B 17/320016 |
| | | | 606/180 |
| 2008/0021488 A1 | 1/2008 | Berberich | |
| 2008/0243153 A1 | 10/2008 | Nguyen et al. | |
| 2011/0196400 A1 | 8/2011 | Robertson et al. | |
| 2012/0239064 A1 | 9/2012 | Cartier et al. | |
| 2013/0274751 A1 | 10/2013 | Steinwachs et al. | |
| 2013/0331833 A1 | 12/2013 | Bloom | |
| 2014/0277040 A1 | 9/2014 | Hayes et al. | |
| 2015/0073418 A1 | 3/2015 | Landes | |
| 2015/0105791 A1 | 4/2015 | Truckai | |
| 2015/0209080 A1 | 7/2015 | Sullivan et al. | |
| 2016/0262769 A1 | 9/2016 | Cragg et al. | |
| 2016/0346036 A1 | 12/2016 | Orczy-Timko et al. | |
| 2017/0056047 A1 | 3/2017 | Keller et al. | |
| 2017/0333127 A1 | 11/2017 | Germain et al. | |
| 2019/0021765 A1 | 1/2019 | Magno et al. | |
| 2019/0105071 A1 * | 4/2019 | Magno, Jr. ....... A61B 17/32056 |
| 2019/0290327 A1 | 9/2019 | Magno et al. | |
| 2019/0298403 A1 | 10/2019 | Willhite et al. | |
| 2019/0321095 A1 | 10/2019 | Germain et al. | |

(Continued)

FOREIGN PATENT DOCUMENTS

EP 1698290 11/2009

*Primary Examiner* — Sarah A Long
(74) *Attorney, Agent, or Firm* — Levine Bagade Han LLP

(57) ABSTRACT

Methods and devices for resecting tissue from the interior of a patient's body using a inner and outer sleeves with respective cutting windows where an inner cutting window includes reinforced section to permit increased sharpness of sections of the inner window.

6 Claims, 13 Drawing Sheets

(56)     References Cited

U.S. PATENT DOCUMENTS

| | | |
|---|---|---|
| 2019/0374246 A1 | 12/2019 | Malkevich et al. |
| 2020/0146703 A1 | 5/2020 | Truckai et al. |
| 2020/0246029 A1 | 8/2020 | Singleton et al. |
| 2020/0405495 A1 | 12/2020 | Gatrell et al. |
| 2021/0007793 A1 | 1/2021 | Germain et al. |
| 2021/0128188 A1* | 5/2021 | Truckai ............ A61B 17/32002 |
| 2021/0169513 A1 | 6/2021 | Wood et al. |
| 2021/0282799 A1 | 9/2021 | Curtin et al. |
| 2022/0047294 A1 | 2/2022 | Truckai et al. |
| 2022/0323073 A1 | 10/2022 | Gurtner et al. |
| 2022/0378457 A1 | 12/2022 | Fugerer et al. |

* cited by examiner

RESECTION DEVICE WITH RAZOR-LIKE CUTTING EDGES

BACKGROUND OF THE INVENTION

Field of the Invention. The present disclosure relates to an instrument and method for resecting tissue from the interior of a patient's body with a motor-driven rotating tubular cutter.

SUMMARY

Some aspects in accordance with principles of the present disclosure relate to a tissue-resecting device for use with a powered surgical tool. The resection device or instrument includes a shaft assembly comprising an outer sleeve and a co-axial inner sleeve. The outer sleeve comprises a tubular member extending distally to a typically rounded distal end, with an outer cutting window in the distal region thereof. The outer window may have a sharp beveled edge but more often has window edges with a plurality of sharp teeth for engaging tissue.

Other aspects in accordance with the present invention relate to features of the inner sleeve in its distal cutting window which will be described further below.

The rotating or oscillating inner sleeve, which is motor-driven, has a distal cutting member or tip which includes a window with cutting edges configured with exceptionally sharp razor-like edge sections. The razor-like edge sections have central portions with an acute sharpness angle is less than 20°, and in some variations less than 15°. In order to strengthen the cutting edges, a plurality of strengthening ribs is provided at the sides of the razor-like edge sections. The strengthening ribs extend annularly to the cutting edge and have an acute sharpness angle at said cutting edge of less than 30°, and in same variations, less than 25°.

The present disclosure includes improved surgical instruments for resecting tissue. In one variation, such a device can include an elongated shaft extending about a longitudinal axis comprising an outer sleeve having an outer cutting window and an inner sleeve having an inner cutting window, the inner sleeve coaxially located within the outer sleeve; wherein the inner cutting window includes a first cutting edge circumferentially spaced apart from a second cutting edge, where the first cutting edge and the second cutting edge both include a plurality of razor edge sections and a plurality of strengthening ribs; and wherein the plurality of strengthening ribs extend along an interior wall of the inner sleeve from the inner cutting window, such that at the first cutting edge and the second cutting edge each razor edge section of the plurality of razor edge sections is adjacent to a cutting region having at least one strengthening rib of the plurality of strengthening ribs, such that a sharpness of each razor edge section is greater than a sharpness of the cutting region.

Variations of the instruments can include devices where the sharpness of at least a portion of one of the plurality of razor edge sections comprises a sharpness angle less than 20 degrees. The surgical instrument can comprise sharpness of at least a portion of one of the cutting regions that comprises an acute sharpness angle of less than 30 degrees.

Additional variations of the instrument can include the interior wall comprising a thickness and wherein the plurality of razor edge sections are formed from a cut-away portion of the interior wall.

Variations of the device can include an axial length of each razor edge section is 6 mm or less. Alternatively, an axial length of each razor edge section can be 4 mm or less. The axial length can be measured as the distance between the ribs or is the thinner section of the wall. Alternatively, the axial length of the razor edge can be measured as the portion of the edge with a consistent angle at the cutting edge.

In an additional variation, an axial length of the inner cutting window is less than 10 mm and each of the first cutting edge and the second cutting edge includes at least two razor edge sections.

The instruments described herein can include a cutting edge boundary of each strengthening rib that has a configuration selected from a round shape, an apex and a flat shape.

The devices described herein can include an acute sharpness angle of the first cutting edge and the second cutting edge can transition smoothly in an axial direction from a sharpness angle of the strengthening rib to a sharpness angle of razor edge sections.

In additional variations, an acute sharpness angle of the first cutting edge and the second cutting edge can transition axially with a discontinuity between a sharpness angle of the strengthening rib and a sharpness angle of razor edge sections.

Another variation of a surgical instrument for resecting tissue can include an elongated shaft comprising an inner sleeve coaxially extending within an outer sleeve, wherein a distal region of the inner sleeve comprises an inner cutting window and a distal region of the outer sleeve comprises an outer cutting window; wherein the inner cutting window includes a first cutting edge circumferentially spaced apart from a second cutting edge; and wherein at the inner cutting window a wall of the inner sleeve comprises a wall thickness, and wherein at the first cutting edge and the second cutting edge a plurality of razor cutting edges are formed by removing a first portion of the wall such that a thickness of each razor cutting edge of the plurality of razor cutting edges is less than the wall thickness.

Variations of the instrument can include devices where a sharpness of the first cutting edge and a sharpness of the second cutting edge both extend over a radial angle of at least 30 degrees.

Additional variations of the device can include a second portion of the wall adjacent to each razor cutting edge of the plurality of razor cutting edges that form a plurality of strengthening ribs having a greater thickness than the thickness of the plurality of razor cutting edges.

The present disclosure also includes methods of resection tissue having selectively sharp cutting regions as described herein that permit relatively slow rotational speeds while providing a higher rate of tissue removal. For example, such a method can include providing a tissue-resecting device with an elongated shaft extending about a longitudinal axis to a working end comprising an inner sleeve co-axial positioned within an outer sleeve, the inner sleeve and the outer sleeve each respectively having an inner cutting window and an outer cutting window, wherein a wall of the inner sleeve proximate to a cutting edge of the inner cutting window is configured with a plurality of strengthening ribs adjacent a plurality of razor edge sections including an acute sharpness angle of less than 20 degrees; positioning the working end against targeted tissue; rotating the inner sleeve at less than 3,000 RPM; and resecting tissue at a rate greater that 5 grams/min.

Another variation of a surgical instrument for resecting tissue can include an elongated shaft comprising an inner sleeve coaxially extending within an outer sleeve, wherein a distal region of the inner sleeve comprises an inner cutting window and a distal region of the outer sleeve comprises an outer cutting window; wherein the inner cutting window includes a first lateral side circumferentially spaced-apart from a second lateral side, where the first lateral side and the second lateral side are each configured to have a wave-shaped cutting edge; and wherein a peak of each wave-shaped cutting edge defines a first acute sharpness angle and a bottom of each wave-shaped cutting edge defines a second acute sharpness angle, the second acute sharpness angle being less than the first acute sharpness angle, wherein the peak of each wave-shaped cutting edge comprises a first thickness that is greater than a second thickness of the bottom of each wave-shaped cutting edge such that an adjacent wall region of the peak of each wave-shaped cutting edge defines strengthens wave-shaped cutting edge on the first lateral side and on the second lateral side.

The peak of each wave-shaped cutting edge can comprise a radius. Alternatively, or in combination, one or more peaks of each wave-shaped cutting edge can comprise a sharp apex.

Other aspects in accordance with the present invention relate to features of the inner sleeve in its distal cutting window which will be described further below.

DETAILED DESCRIPTION

Surgical probes of the present disclosure may be utilized in various types of surgeries, including but not limited to gynecology procedures such a myomectomies and polypectomies, and also can be used in ENT procedures, arthroscopies, spine surgeries, tumor resection procedures and the like.

Figure 1:
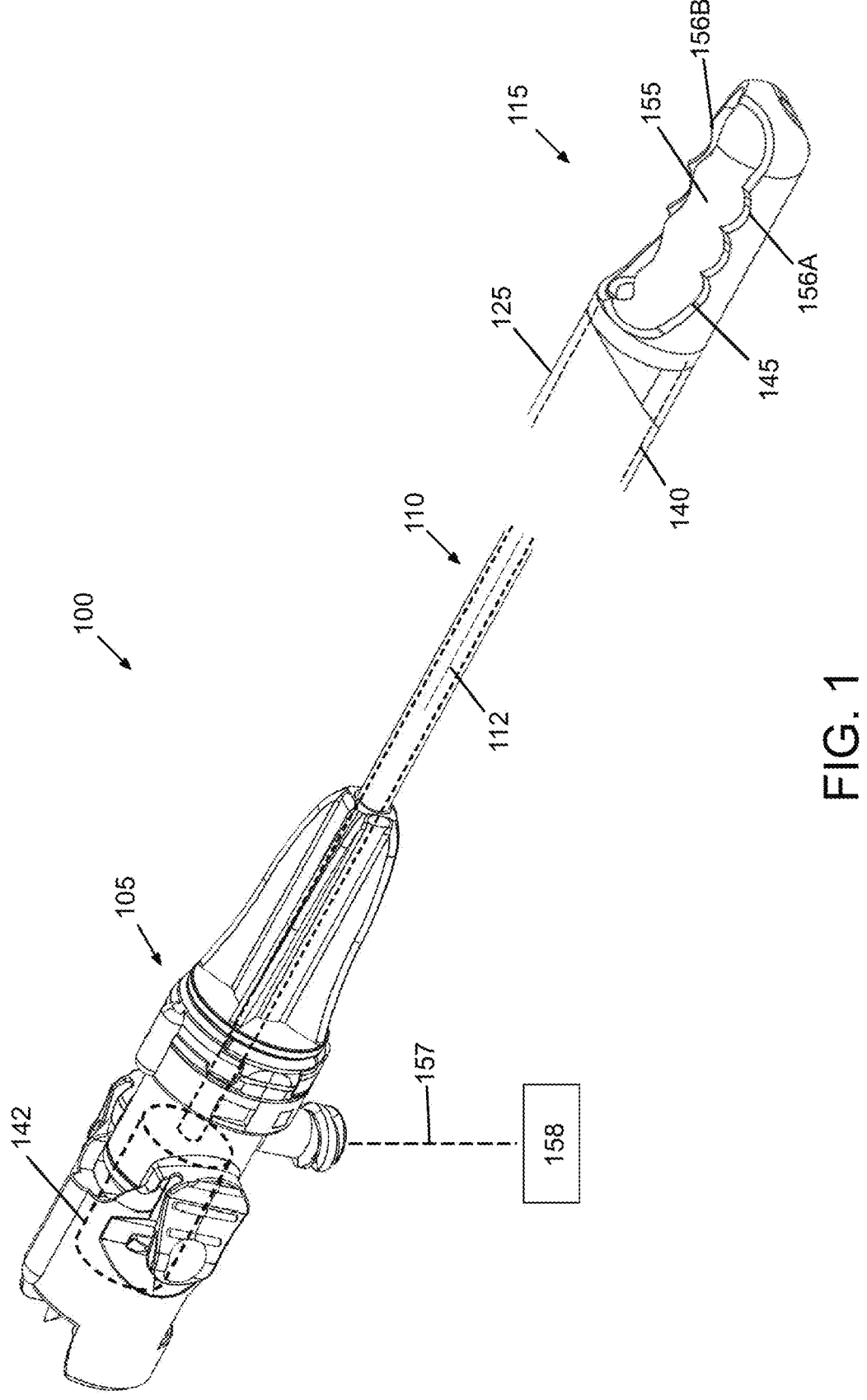
FIG. 1 is a perspective view of a surgical cutting device or blade corresponding to the invention that is adapted for resecting and removing tissue from a patient's body, wherein and elongate shaft portion of the probe includes a windowed outer sleeve and a rotatable windowed inner sleeve that can be rotated or rotationally oscillated.
Figure 2A:
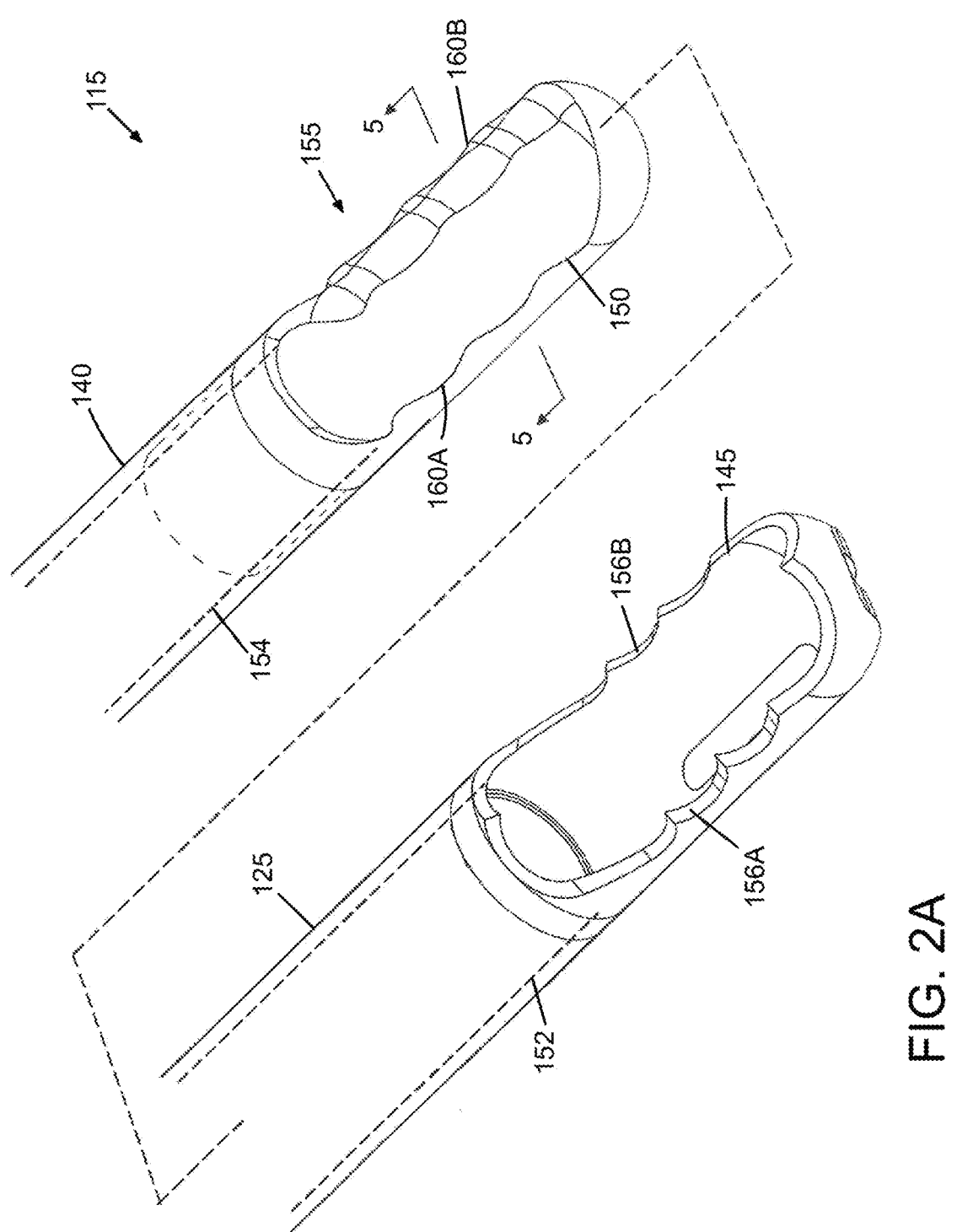
FIG. 2A is a perspective view of the outer and inner sleeves of the device of FIG. 1 separated from one another.

A surgical cutting probe 100 in accordance with aspects of the present invention is shown in FIGS. 1 and 2A. The cutting probe 100 includes a proximal hub 105 coupled to an elongate shaft assembly 110 extending about longitudinal axis 112 to a distal working end 115. The hub 105 can be detachably coupled to a handpiece that carries a motor drive (not shown) as is known in the art.

The probe 100 and its shaft 110 include co-axial outer and inner sleeves 125 and 140, respectively, wherein the inner sleeve 140 is rotatable by the motor drive. The inner sleeve 140, also called a blade, includes an inner hub member 142 that rotates within the proximal hub 105 (FIG. 1) as is known in the art. The outer sleeve 125 has a distal portion with a cutting window 145 therein. The inner sleeve 140 has a cooperating distal inner cutting window 150 which rotates within the bore 152 of the outer sleeve 125 (FIG. 2A).

The handpiece and motor drive are adapted for driving the rotational movement of the inner sleeve 140 and a distal cutter portion 155 thereof which carries the inner cutting window 150. The handpiece also is configured with an aspiration channel that couples to the aspiration passageway or bore 154 in the inner sleeve 140 for extracting fluids and tissue chips from a resection site in a patient's body (FIG. 2A). Thus, the inner cutting window 150 of inner sleeve 140 functions as a fluid outflow port communicating with the inner sleeve bore 154 that is coupled through tubing 157 to a remote negative pressure source 158 (FIG. 1).

Optionally, a fluid inflow path can be provided to the proximal hub 105 of the probe 100 to deliver fluid to the annular space between the inner and outer sleeves, 125 and 140, so that the window 145 of the outer sleeve 125 functions as a fluid inflow port. Such a fluid inflow path, in turn, would be is adapted for connection to inflow tubing (not shown) that is coupled to a pressurized fluid source.

Figure 3A:
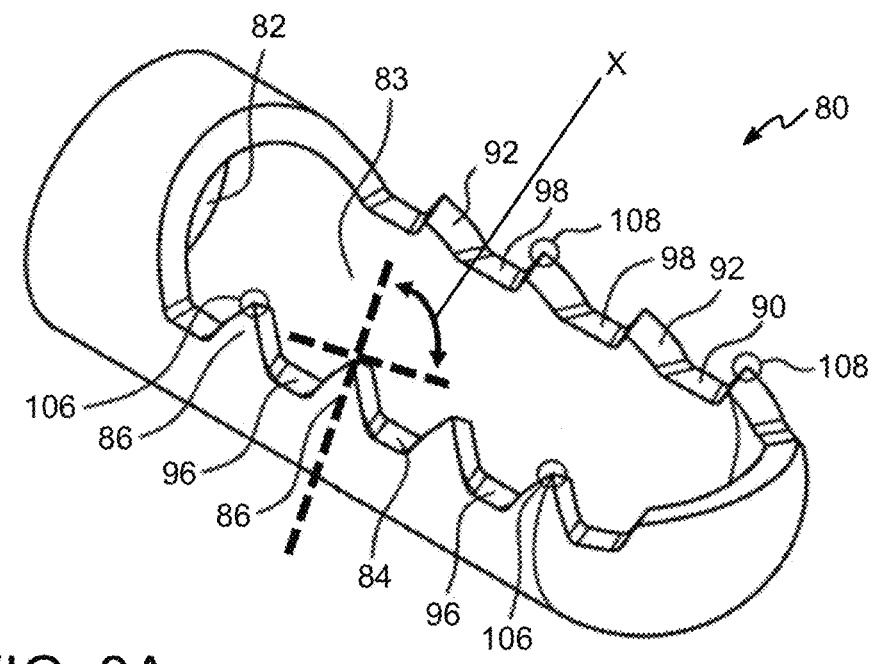
FIG. 3A is a perspective view of a prior art inner sleeve cutting window of a tubular cutter which illustrates typical cuttings edges that do not have a sharp cutting angle.
Figure 3B:
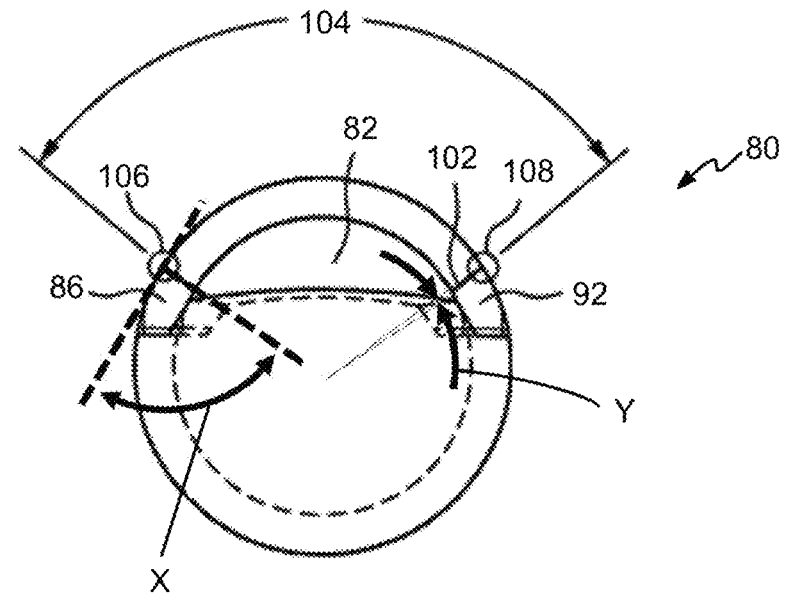
FIG. 3B is a cross-sectional view of the cutting member of FIG. 2A.

After understanding the general principles of the probe 100, several particular features of the working end 115 of FIGS. 1 and 2A are shown in greater detail in FIGS. 4, 5, 6A, 6B and 7 which can be compared to a prior art working end shown in FIGS. 3A and 3B. The prior art illustrations of FIGS. 3A and 3B are reproductions of FIGS. 19 and 20 from European Patent Specification EP1698290B1 filed Feb. 3, 2006 by Van Wyk, also published as US Patent Application 20060196038.

In FIG. 2A, the inner sleeve 140 and its distal cutter portion 155 are shown separated from the outer sleeve 125. In general terms, the inner sleeve 140 and cutter portion 155 are rotatably disposed within the bore 152 in the outer sleeve 125 such that the inner cutting window 150 rotates or oscillates to cut or shear tissue captured against the cutting edges 156A and 156B of the outer sleeve cutting window 145 (see FIGS. 1 and 2A).

As it can be seen in FIGS. 2B, 4, 5, 6A and 6B, the inner cutting window 150 has circumferentially spaced-apart first and second cutting edges 160A and 160B that are exceptionally sharp, with highly acute cutting angles, compared to the cutting edges of typical prior art cutters as shown in FIGS. 3A-3B. In the prior art, the typical teeth 92 of an inner sleeve of a working end 80 as shown in FIGS. 3A and 3B have crests of any cutting edges or teeth that are not particularly sharp. As can be seen in FIGS. 3A and 3B, the acute cutting angle X of the tip 106 of the teeth is 92 is close to 90°. In use, such teeth are rotated at high speed, for example, from 3,000 RPM to 15,000 RPM, where the teeth essentially tear tissue rather than slicing into and cutting tissue.

Now referring to FIGS. 4 to 6B, the cutting edges 160A and 160B of the inner sleeve cutter portion 155 shown in FIGS. 1 and 2B have first and second alternating axial edge portions (wave crest or peak section 165 and wave bottom section 175) with extremely acute cutting angles that are less than 30° and less than 20°, respectively, as will be described further below. It has been found that the sharp cutting edges of such an inner sleeve can be operated at slow speeds, for example from 1,000 RPM to 3,000 RPM, and provide higher tissue removal rates in terms of grams/min of tissue removal, than high speed, dull cutters known in the art.

It can be understood how sharper cutting edges will cut tissue better than duller cutting edges. However, sharper edges can be weaker and prone to deformation and flexing. When using a rotating inner sleeve 140 of the type shown in FIG. 2B, it can be understood that if a thin, sharp cutting edge is flexed outwardly, for example when engaging dense tissue, then an inner sleeve cutting edge (160A, 160B) could strike an edge (156A, 156B) of the outer sleeve window 145 and damage or break the blade.

Figure 4:
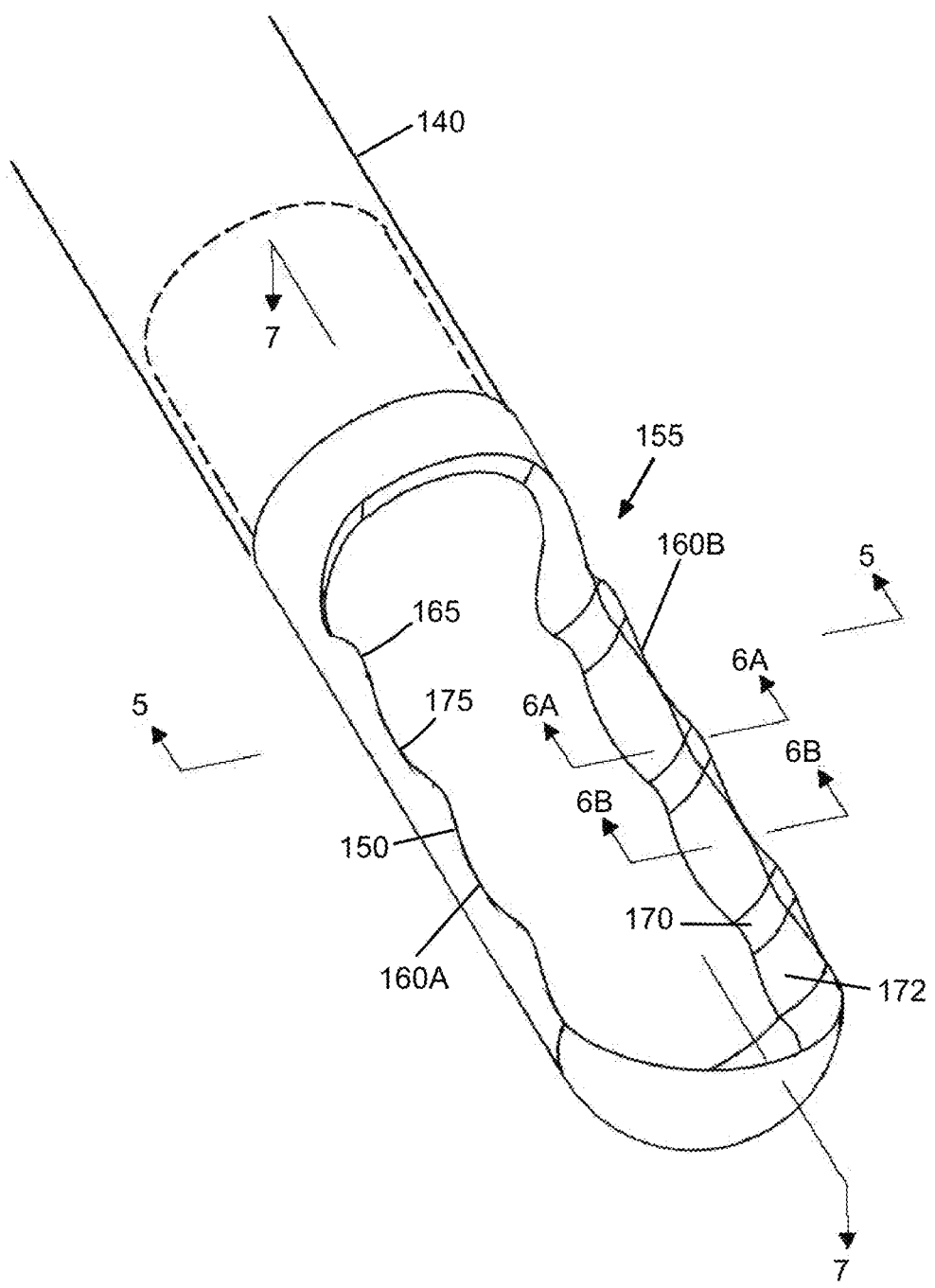
FIG. 4 is a perspective view of the inner sleeve and its distal cutter portion illustrating the configuration of its cutting window with a plurality of razor-like cutting edges sections intermediate a plurality of strengthening rib elements.
Figure 7:
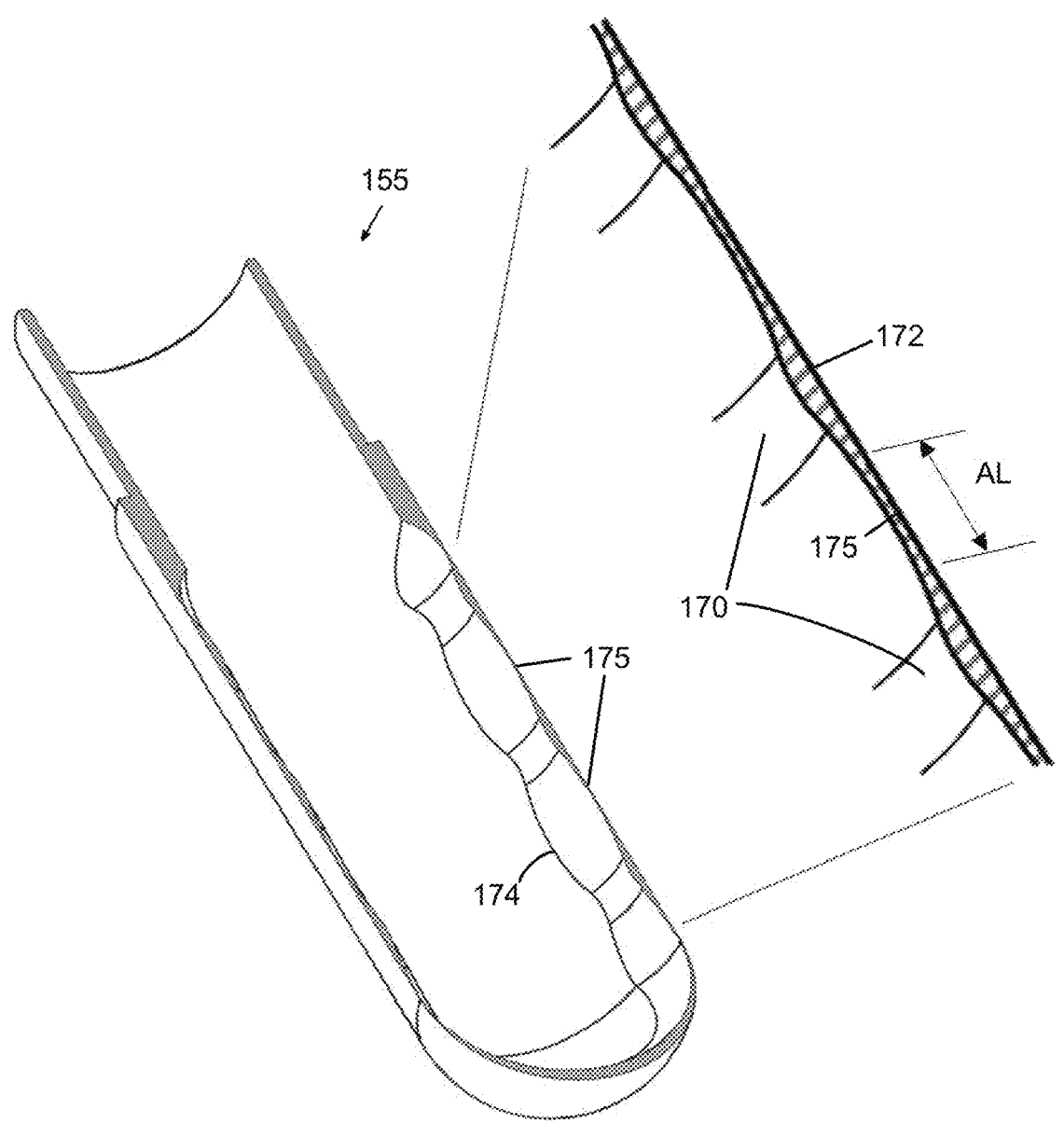
FIG. 7 is a longitudinal sectional view of cutter portion of FIG. 4 taken along line 7-7 of FIG. 4 showing the strengthening ribs of the cutter.

As can best be seen in FIGS. 4 and 7, the inner sleeve cutter portion 155 of the invention is configured with a plurality of partly annular strengthening portions or ribs 170 such that axial bottom sections 175 of the cutting edges 160A and 160B intermediate the ribs 170 can have a highly sharpened cutting edge and yet the overall cutting edge will be strong enough to prevent edge deformation or flexing during use.

Figure 5:
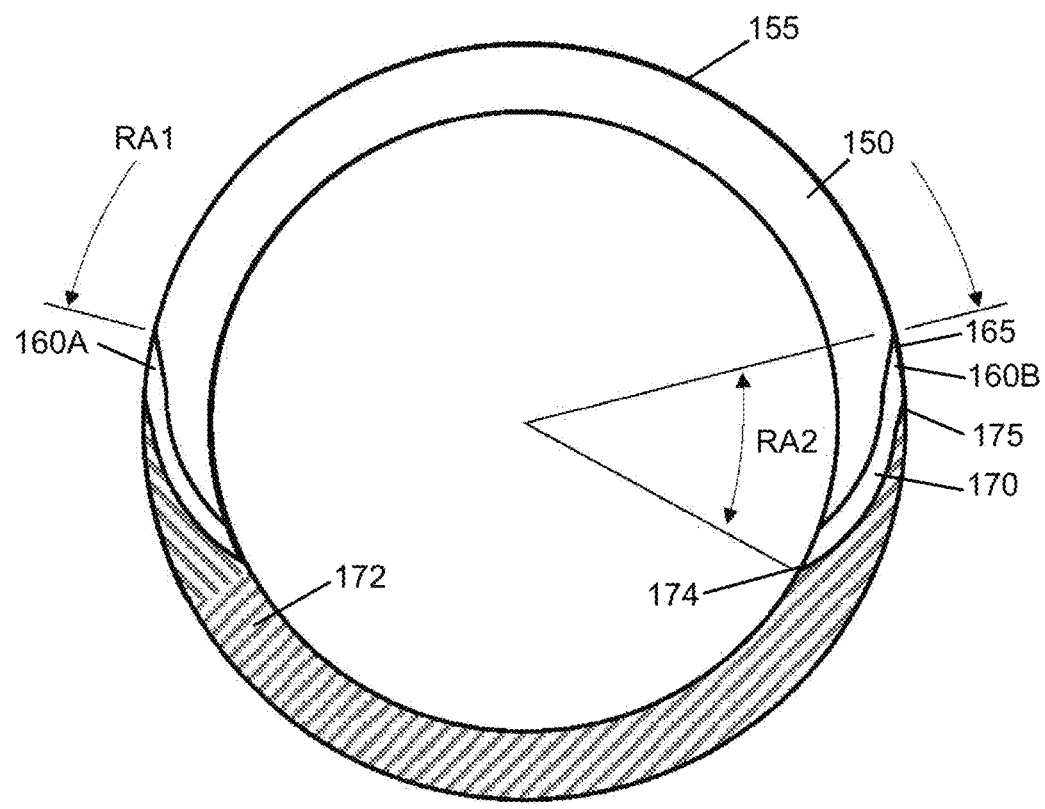
FIG. 5 is a cross-sectional view of the distal cutter portion of the inner sleeve of FIG. 4 taken along line 5-5 of FIGS. 2B and 4.

More in particular, in a variation shown in FIG. 2B and FIGS. 4-6B, the inner cutting window 150 has an axial length from 6 mm to 12 mm, and typically less than 10 mm. In a specific example, the length of the inner cutting window 150 is 8.5 mm. The window 150 and cutting edges 160A and 160B have an undulating, wave-like configuration with at least two wave crests or peaks 165 or teeth with adjacent or intermediate bottom sections 175. In one variation, the inner sleeve 140 has an outer diameter of less than 3.5 mm and in a specific example is 3.385 mm with an inner diameter of 2.8 mm, and a cutter wall 172 having a thickness of 0.585 mm. As also can be seen in FIG. 5, the radial angle RA1 of the window 150, between opposing wave crests, is typically greater than 145° and in a specific variation is 156.4°. The acute cutting edges 160A and 160B are provided by grinding or milling the inner surface of the wall 172 by a large amount as indicated by the cut-away angle RA2 of at least 30° as shown in FIG. 5. The cut-away radial angle RA2 is defined by the angle between to wave crest 165 and the point 174 where the cutter wall 172 is not milled away or reduced in thickness. In a particular variation, the cut-away radial angle RA2 is 41° which is very large when compared to prior art cutters. In the prior art cutter of FIGS. 3A and 3B, it can be seen that the corresponding cut-away radial angle Y is in the range of 0° (zero degrees), which is another way to define the sharpness of the cutting edges 160A and 160B.

Figure 6A:
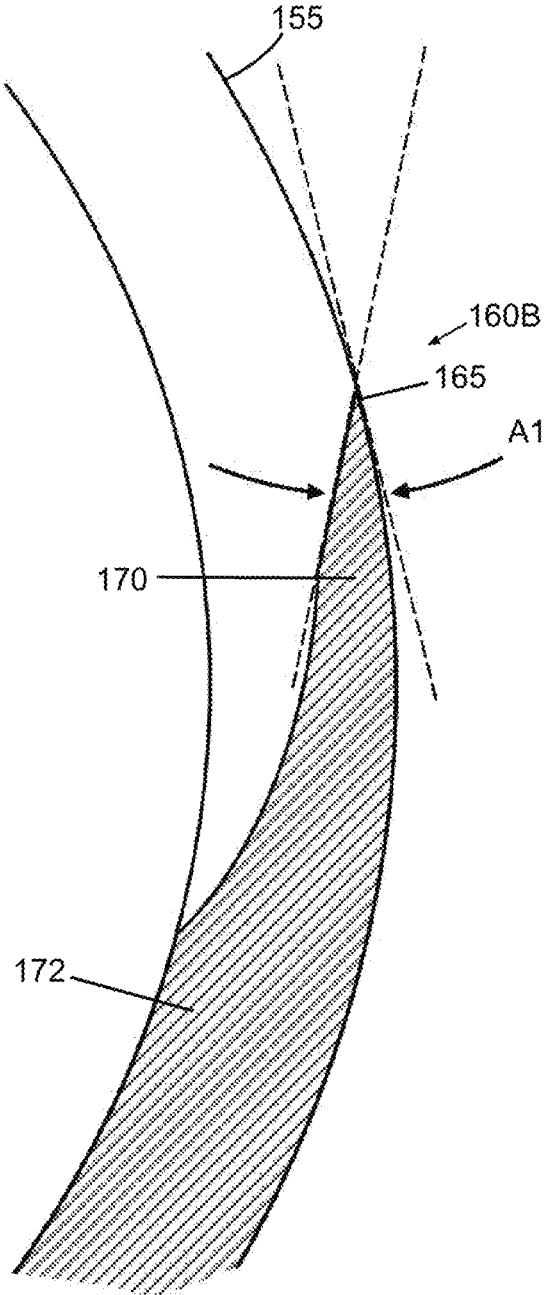
FIG. 6A is a greatly enlarged cross-sectional view of the cutting edge of FIG. 4 taken along line 6A-6A of FIG. 4 showing the acute sharpness angle of the boundary of a strengthening rib of the wave-like cutting edge.
Figure 6B:
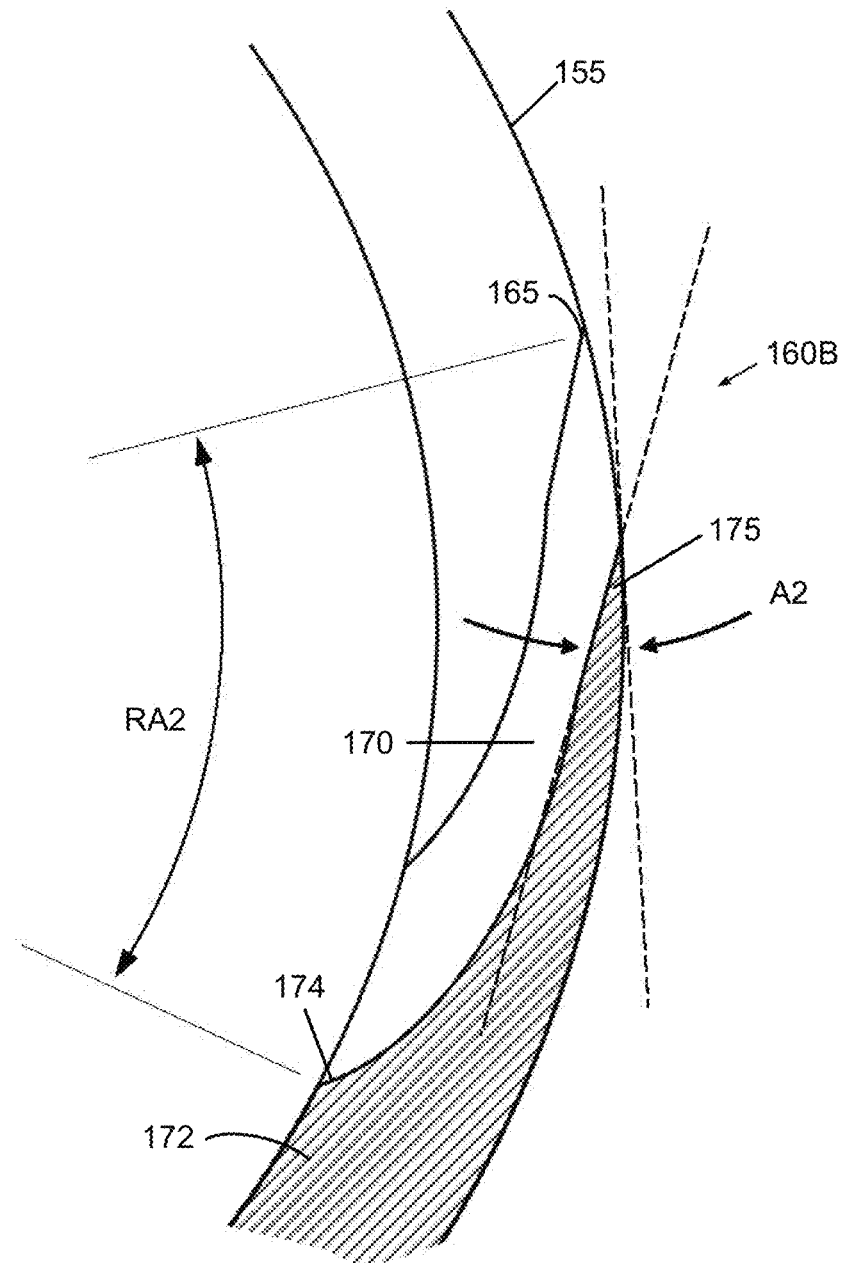
FIG. 6B is an enlarged cross-sectional view of the cutting edge of FIG. 4 taken along line 6B-6B of FIG. 4 showing the acute sharpness angle of the bottom of the wave-like cutting edge.

Now turning to FIGS. 4 and 7, the strengthening ribs 170 extend annularly to an upper termination or boundary at the wave crest 165 or peak of the undulation. The sharpness angle or cutting angle A1 at each crest 165 is less than 30°, and often less than 25°, as shown in FIG. 6A. In a specific example shown in FIGS. 5 and 6A, the cutting angle A1 at the crest 165 is 23.77°. Referring again to FIGS. 2B and 4, the trough or bottom section 175 of each wave or undulation has a razor-like configuration with a highly acute sharpness angle A2 of less than 20°, and often less than 15°, as shown in FIG. 6B. In a specific example shown in FIG. 6B, the cutting angle A2 at the wave edge bottom 175 is 14.16°. It has been found that strengthening ribs 170 on either side of a shortened wave bottom section 175 will allow for a highly acute sharpness angle A2 in such a bottom section 175 wherein the shorter axial length AL of the section will prevent its deformation or flexing during use (FIG. 7). In this variation the axial length AL of the bottom section 175 between ribs 170 is less than 6 mm, and often less than 4 mm. In the variation of FIGS. 2B, 4 and 7, the axial length AL of the bottom section 175 between ribs 170 can generally be defined relative to the height B of the undulation, where the bottom section 175 extends axially over the region where height C is less than 50% of the total wave height B. It should be appreciated that the lesser sharpness angle A1 in the crest section 165 and the inner surface of the strengthening ribs 170 can transition smoothly to the higher sharpness angle A2 of the wave bottom, as can be best seen in FIGS. 4 and 7. In other variations shown in FIGS. 9 and 10, the transition between the strengthening ribs 200 and 210 and the higher sharpness angle A2 of the intermediate bottom section 195, 205 can be without a smooth transition and instead have an angular transition 177.

Figure 2B:
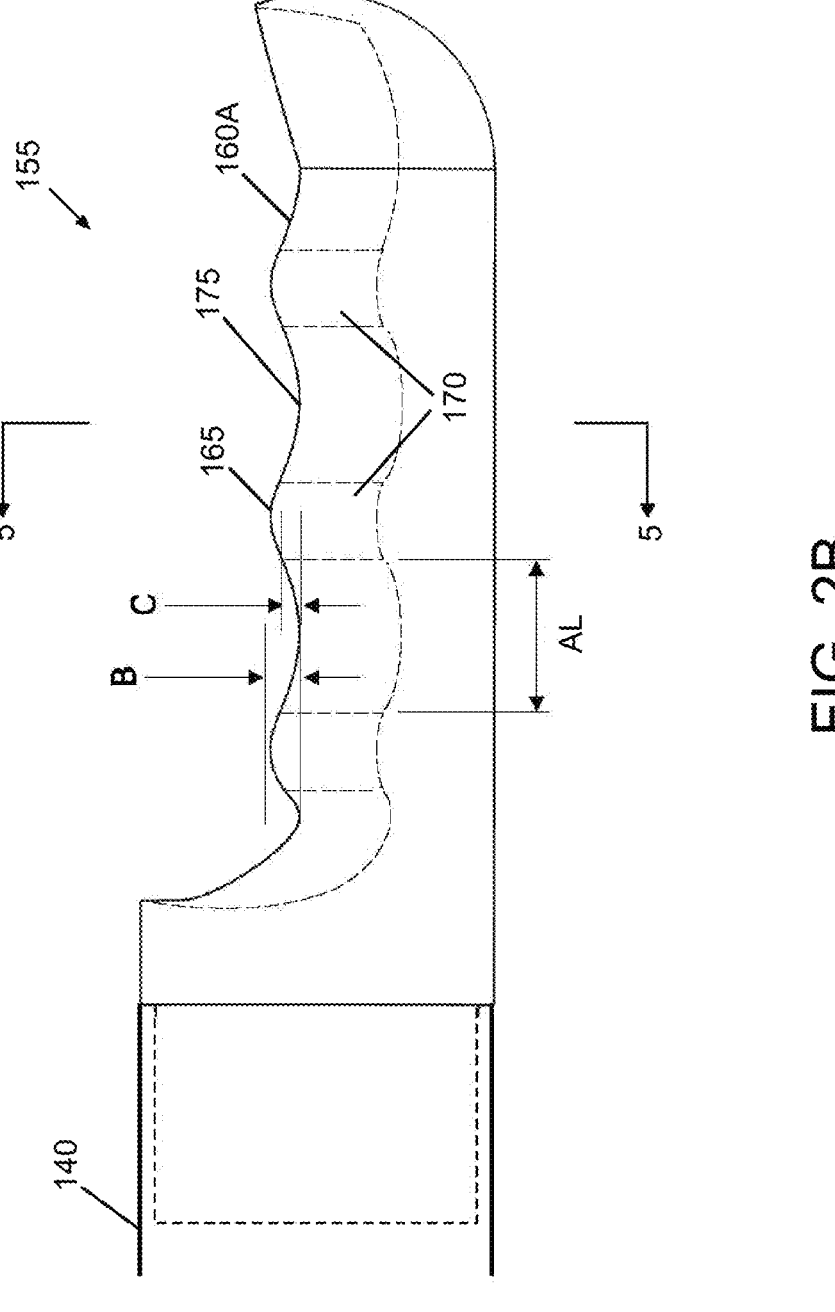
FIG. 2B is a side elevational view of the inner sleeve and inner cutting window of the device of FIG. 1.
Figure 8:
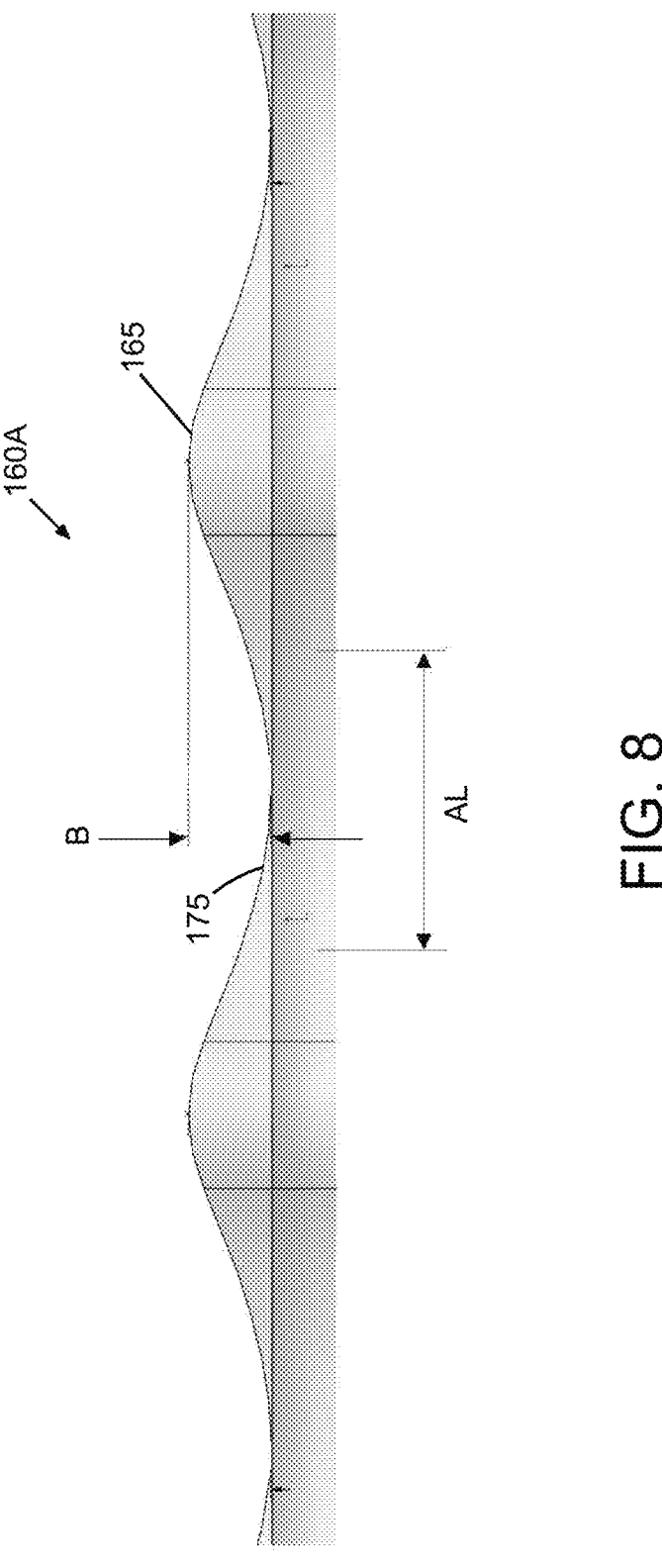
FIG. 8 is an elevational view of a portion of the wave-like configuration of the cutting edge of the cutter of FIGS. 2A-6B.

FIG. 8 illustrates a portion of the wave-like cutting edge 160A of FIGS. 2B and 4 and indicates the height A of the undulations from the wave crest 165 to the bottom 175 of the undulation which can range from zero to 1.5 mm and is one variation is 0.47 mm. FIG. 8 also shows the axial dimension AL of the razor-like edge portion, which as stated above is less than 6 mm and often less than 4 mm.

In one aspect, the invention comprises a tubular cutter with outer and inner sleeves having respective outer and inner cutting windows in distal ends thereof, wherein the inner sleeve is motor-driven to resect tissue, and wherein the inner cutting window has cutting edges that are configured with strengthening ribs adjacent a plurality of razor-like edge sections 175. In this variation, the razor-like edge sections have central portions with an acute sharpness angle is less than 20°. Further, in this variation, the strengthening ribs 170 extend annularly to the cutting edge and have an acute sharpness angle at said cutting edge of less than 35°.

In another aspect, the invention comprises a tubular cutter with outer and inner sleeves having respective outer and inner cutting windows in distal ends thereof, wherein the inner sleeve is motor-driven to resect tissue, and wherein the inner cutting window has exceptionally sharp cutting edges, wherein the inner sleeve wall has a selected thickness, and the sharpness of the cutting edge is defined by a cut-away portion of the wall extending away from an apex of the cutting edge, and where said cut-away portion extends over a radial angle of at least 30°.

As is well known in the field of tissue resection, tubular cutters work optimally when the rotating inner sleeve and inner cutting window 150 oscillates, for example, with 1 to 3 revolutions in one rotational direction followed by a similar number of rotations in the opposite direction. The cutting probe 100 described above typically uses such oscillation to provide improved cutting performance. A gear mechanism to provide such oscillation is described in commonly owned U.S. patent application Ser. No. 16/678,647 titled ENDOSCOPE AND METHOD OF USE filed Nov. 8, 2019, which is incorporated herein by reference. Such a gear mechanism can operate at any suitable rotation speed, for example 100 RPM to 5000 RPM or more.

In another aspect, a method of the invention comprises providing a tubular cutter with outer and inner sleeves having respective outer and inner cutting windows in distal ends thereof, wherein the inner sleeve is motor-driven and oscillates to resect tissue at slow speeds in the range of 500 RPM to 3,000 RPM, and wherein the inner cutting edges have alternating razor-like sections and strengthening rib sections, where the razor-like edge sections have central portions with an acute sharpness angle of less than 20°, and where the strengthening ribs have an acute sharpness angle at said cutting edge of less than 30° and in one variation is less than 25°. At slow speeds in the range of 500 RPM to 3,000 RPM, this variation of cutter, with an inner sleeve having an outer diameter of 3.5 mm or less with a cutting window having an axial length of 10 mm or less, can resect tissue at the rate of at least 5 grams/minute. In a variation, the tissue resection rate is at least 10 grams/minute.

Figure 9:
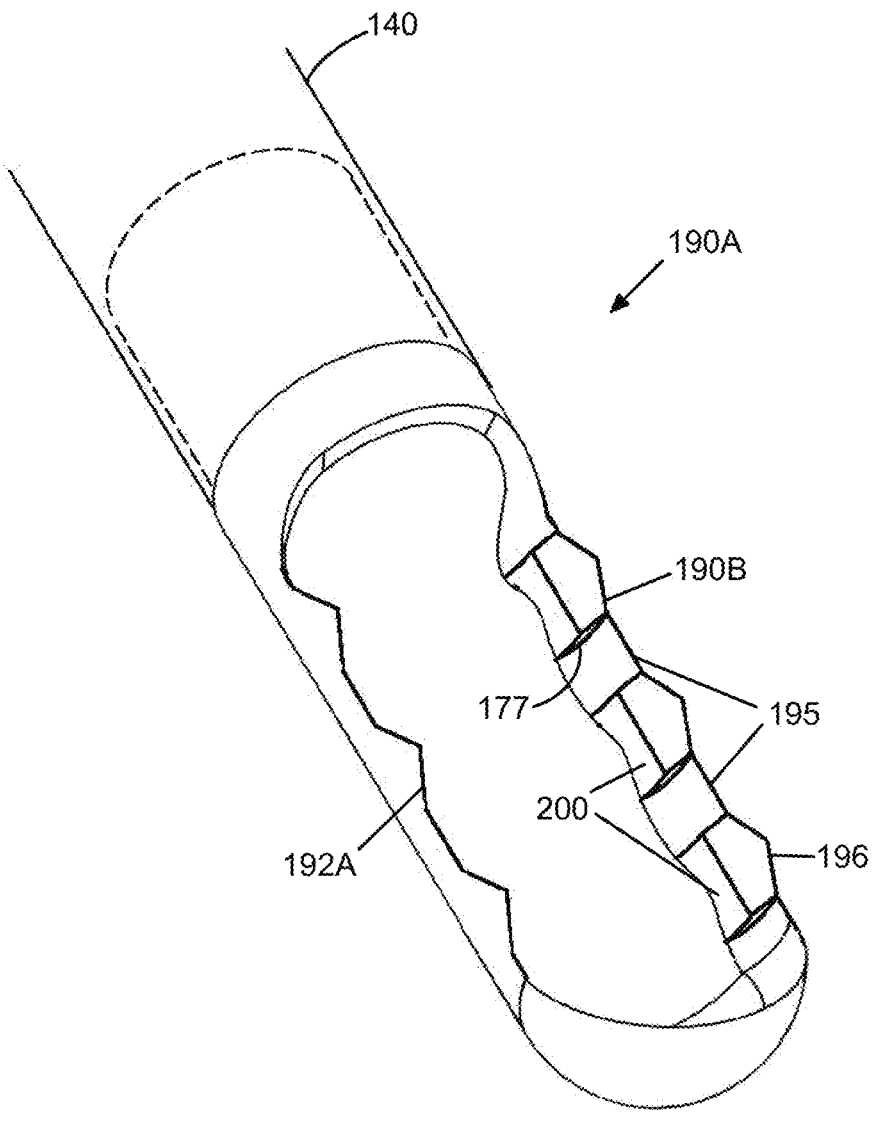
FIG. 9 is a perspective view of another variation of an inner sleeve and distal cutter portion illustrating a cutting window with a differently shaped razor-like cutting edge sections and strengthening ribs.
Figure 10:
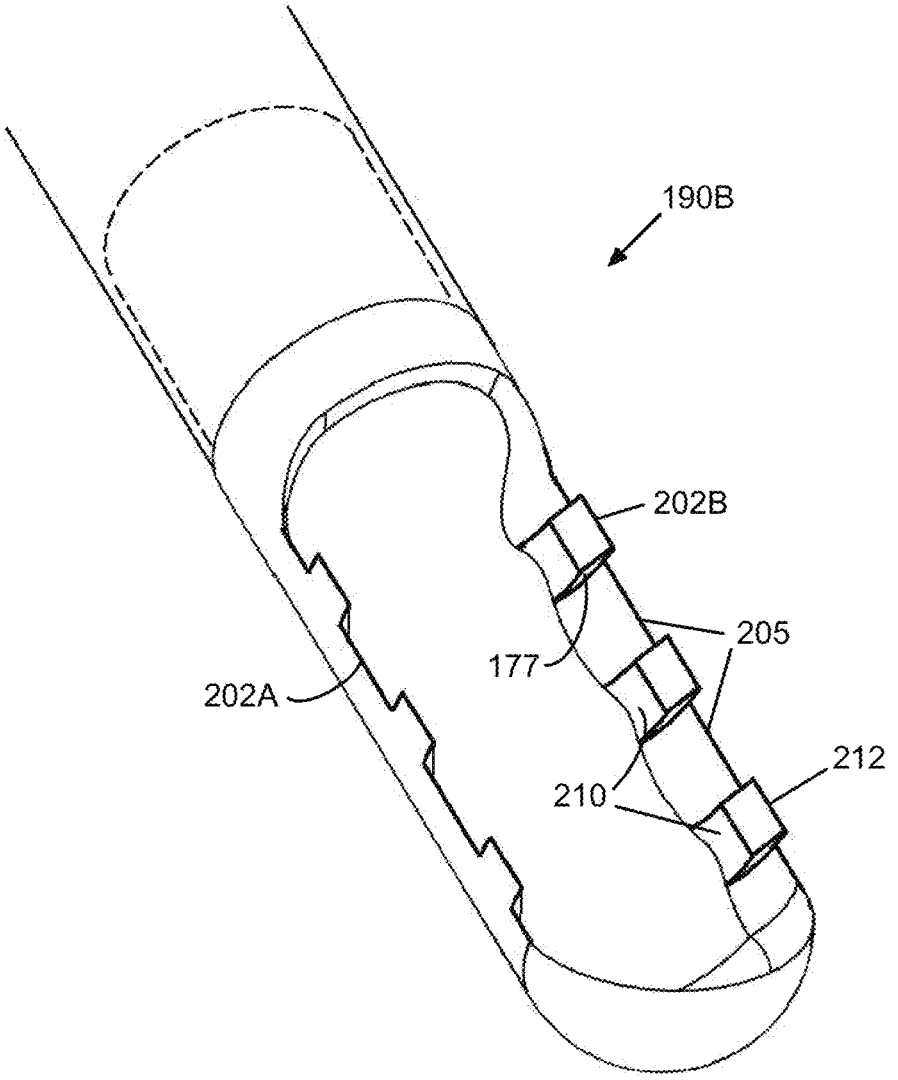
FIG. 10 is a perspective view of another variation of an inner sleeve and distal cutter portion with a different of razor-like cutting edge sections and strengthening ribs.

Now referring to FIGS. 9-10, variations of inner sleeve cutters 190A and 190B are shown. In FIG. 9, the cutting edges 192A and 192B are more angular than the previous variation as shown in FIGS. 2B and 4. In FIG. 9, the razor-like edge sections 195 have a flat (or axis-parallel) cutting edge with a consistent angle over said edge of than less than 20°, or less than 15°, and where the strengthening ribs 200 have a triangular shape, with an apex 196 at the cutting edges with an acute sharpness angle of less than 30° and in one variation less than 25°.

FIG. 10 illustrates a cutter 190B with cutting edges 202A and 202B that are again configured with razor-like edge sections 205 that have a flat or axis-parallel sharp cutting edge having an acute angle of than 20°, or less than 15°. In this variation, the strengthening ribs 210 are configured with a chisel tip 212 at the cutting edges 202A and 202B which again have an acute sharpness angle of less than 30° and in a variation is less than 25°.

Figure 11:
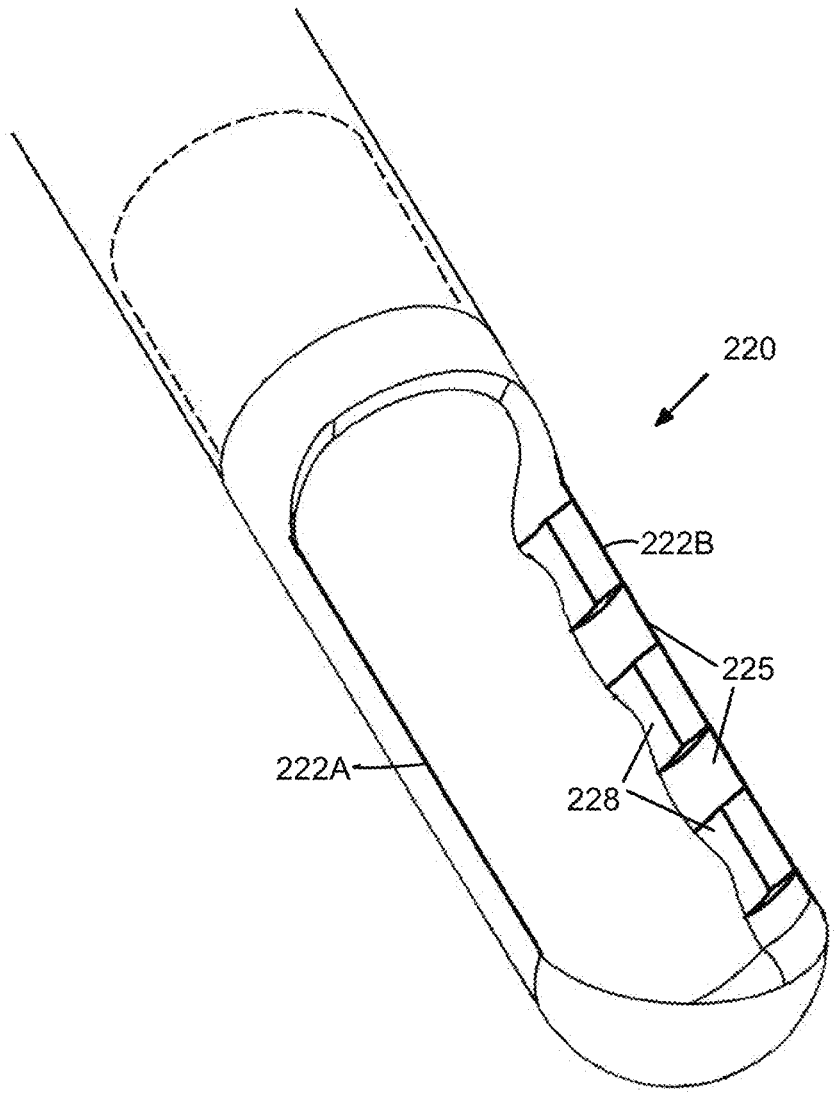
FIG. 11 is a perspective view of yet another variation of a sleeve and distal cutter portion illustrating different razor-like cutting edge sections and strengthening ribs.

FIG. 11 illustrates another variation of inner sleeve cutter 220 with flat cutting edges 222A and 222B with razor-like edge sections 225 that again have an acute angle of than 20°, or less than 15°. In this variation, the strengthening ribs 228 terminate at the flat cutting edges 222A and 222B but function as described previously to strengthen the edges and prevent flexing of the razor-like edge sections 225.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A surgical instrument for resecting tissue, comprising:
an elongated shaft comprising an inner sleeve coaxially extending within an outer sleeve, wherein a distal region of the inner sleeve comprises an inner cutting window and a distal region of the outer sleeve comprises an outer cutting window;
wherein the inner cutting window includes a first lateral side circumferentially spaced-apart from a second lateral side, where the first lateral side and the second lateral side are each configured to have a wave-shaped cutting edge; and
wherein a peak of each wave-shaped cutting edge defines a first acute sharpness angle and a bottom of each wave-shaped cutting edge defines a second acute sharpness angle, the second acute sharpness angle being less than the first acute sharpness angle, wherein the peak of each wave-shaped cutting edge comprises a first thickness that is greater than a second thickness of the bottom of each wave-shaped cutting edge such that an adjacent wall region of the peak of each wave-shaped cutting edge strengthens the wave-shaped cutting edges on the first lateral side and on the second lateral side.

2. The surgical instrument of claim 1, wherein the second acute sharpness angle is at least 5 degrees sharper than the first acute sharpness angle.

3. The surgical instrument of claim 2, wherein the second acute sharpness angle is at least 10 degrees sharper than the first acute sharpness angle.

4. The surgical instrument of claim 1, wherein the second acute sharpness angle is less than 20 degrees.

5. The surgical instrument of claim 1, wherein the peak of each wave-shaped cutting edge comprises a radius.

6. The surgical instrument of claim 1, wherein the peak of each wave-shaped cutting edge comprises a sharp apex.

* * * * *